US012710482B2

(12) United States Patent
Batchelor et al.

(10) Patent No.: US 12,710,482 B2
(45) Date of Patent: Aug. 18, 2026

(54) CURRENT LEAKAGE TECHNIQUES FOR RADIO FREQUENCY INSTRUMENTS

(71) Applicant: GYRUS ACMI, INC., Westborough, MA (US)

(72) Inventors: Kester Julian Batchelor, Mound, MN (US); Kevin Roy Aufderhar, Coon Rapids, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 1063 days.

(21) Appl. No.: 17/451,016

(22) Filed: Oct. 15, 2021

(65) Prior Publication Data

US 2022/0120824 A1 Apr. 21, 2022

Related U.S. Application Data

(60) Provisional application No. 63/092,925, filed on Oct. 16, 2020.

(51) Int. Cl.

| | |
|---|---|
| ***G01R 31/52*** | (2020.01) |
| ***A61B 18/12*** | (2006.01) |
| ***A61B 18/14*** | (2006.01) |
| *A61B 17/00* | (2006.01) |
| *A61B 18/00* | (2006.01) |

(52) U.S. Cl.

CPC .......... *G01R 31/52* (2020.01); *A61B 18/1233* (2013.01); *A61B 18/1445* (2013.01); *A61B 2017/00725* (2013.01); *A61B 2018/00595* (2013.01); *A61B 2018/00601* (2013.01); *A61B 2018/00827* (2013.01); *A61B 2018/00892* (2013.01); *A61B 2018/00898* (2013.01); *A61B 18/1206* (2013.01)

(58) Field of Classification Search

CPC . G01R 31/52; A61B 18/1233; A61B 18/1445; A61B 18/1206; A61B 2017/00725; A61B 2018/00595; A61B 2018/00601; A61B 2018/00827; A61B 2018/00892; A61B 2018/00898; A61B 18/14; A61B 18/12

See application file for complete search history.

(56) References Cited

U.S. PATENT DOCUMENTS

| | | | | |
|---|---|---|---|---|
| 4,200,105 A * | 4/1980 | Gonser | .................... | H02H 3/05 606/35 |
| 7,766,905 B2 * | 8/2010 | Paterson | ................ | G01R 31/52 606/34 |
| 2006/0041252 A1 * | 2/2006 | Odell | ..................... | A61B 90/06 606/34 |

(Continued)

*Primary Examiner* — Joanne M Rodden
*Assistant Examiner* — Dana Stumpfoll
(74) *Attorney, Agent, or Firm* — Schwegman Lundberg & Woessner. P.A.

(57) ABSTRACT

Techniques for detecting leakage current of an electrosurgical instrument are provided. In an example, a method of operating an electrosurgical instrument can include applying a radio frequency (RF) signal to electrode conductors of the electrosurgical instrument, determining leakage current of an leakage conductor coupled to the electrosurgical instrument exceeds a first threshold, and providing a first indication in response to the determining the leakage current of the leakage conductor exceeds the first threshold.

12 Claims, 6 Drawing Sheets

(56) References Cited

U.S. PATENT DOCUMENTS

| | | | | |
|---|---|---|---|---|
| 2006/0247508 | A1* | 11/2006 | Fennell | G01R 31/52<br>600/365 |
| 2012/0123408 | A1* | 5/2012 | Zoran | A61B 18/1233<br>606/41 |
| 2015/0359584 | A1* | 12/2015 | Newton | A61B 18/1233<br>606/34 |
| 2016/0192980 | A1* | 7/2016 | Newton | A61B 90/98<br>606/34 |
| 2020/0281643 | A1* | 9/2020 | Nussbaum | A61B 18/1206 |

* cited by examiner

CURRENT LEAKAGE TECHNIQUES FOR RADIO FREQUENCY INSTRUMENTS

CROSS-REFERENCE TO RELATED APPLICATION

This application claims the benefit of priority to U.S. Provisional Patent Application Ser. No. 63/092,925, filed Oct. 16, 2020, the contents of which are hereby incorporated by reference in their entirety.

FIELD OF THE DISCLOSURE

The present invention relates to medical procedure instruments and, more particularly to techniques for detecting current leakage of radio frequency (RF) instruments.

BACKGROUND OF THE DISCLOSURE

Medical instruments can include electrodes and drivers for delivering RF energy to an anatomical target. The RF energy can provide a variety of medical benefits. As with most instruments, or tools, time can affect the efficiency of delivering the benefit of the tool. For example, repeated use or exposure to various elements can degrade the efficiency of the instrument. For RF instruments, one aspect of the instrument that is not immune to degradation is the insulation of the conductor(s) coupling the RF energy source with the RF electrodes.

SUMMARY OF THE DISCLOSURE

Techniques for detecting leakage current of an electrosurgical instrument are provided. In an example, a method of operating an electrosurgical instrument can include applying a therapy signal to electrode conductors of the electrosurgical instrument, determining leakage current of an leakage conductor coupled to the electrosurgical instrument exceeds a first threshold, and providing a first indication in response to the determining the leakage current of the leakage conductor exceeds the first threshold.

This section is intended to provide an overview of subject matter of the present patent application. It is not intended to provide an exclusive or exhaustive explanation of the invention. The detailed description is included to provide further information about the present patent application.

DETAILED DESCRIPTION

Figure 1:
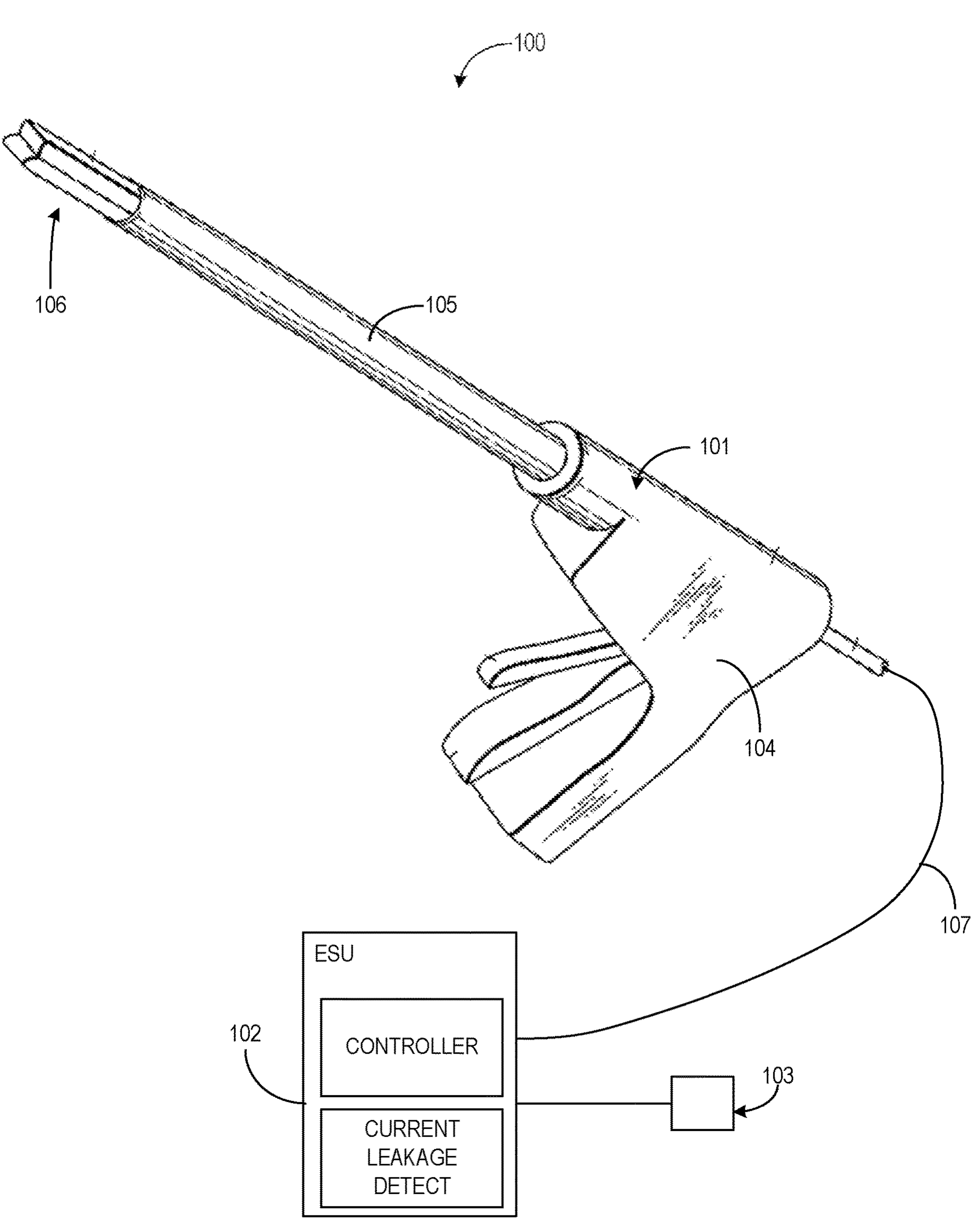
FIG. 1 illustrates generally an example system according to the present subject matter.

FIG. 1 illustrates generally an example system 100 according to the present subject matter. The system can include an RF instrument 101, an energy source 102 or electrosurgical unit (ESU), and an optional footswitch 103. The RF instrument 101 can include a handle 104, a shaft 105, and an end-effector 106. The handle 104 can be connected with the energy source 102 through a cable 107. The footswitch 103, which can be a hand switch in some examples, can be connected with the energy source 102. In certain examples, when an end-user operates a pedal of the footswitch 103, the turning on/off of the supply of energy to the RF instrument 101 from the energy source 102 is controlled. For example, when the pedal is pressed, an output is produced based on a state where radio-frequency energy is appropriately set. When the pedal is released, an output of the radio-frequency energy is stopped.

In certain examples, the handle 104 can be formed into a shape that can be easily grasped by an operator. The shaft 105 is arranged on one end of the handle 104. The cable 107 can extend from the one end of the handle 104 coaxially with the shaft 105. The cable 107 can include a number of conductors for conducting RF signals to one or more RF electrodes mounted to the end effector 106. The handle 104 can include one or more handle levers for controlling the orientation or actuation of the end effector 106. In some examples, the end effector 106 can include a single electrode (not shown) extending from the end of the shaft 105. In some examples, one or more levers of the handle 104 can allow for the electrode to be extended and retracted relative to the end of the shaft 105. In some examples, a lever can allow for the electrode to be rotated or hinged. In some examples, the end effector 106 can include two electrodes (not shown) with a first electrode mounted on a first jaw of the end-effector 106 and a second electrode mounted on a second jaw of the end-effector 106. In such an example, and in addition to functions discussed above with respect to a single electrode end-effector, a lever of the handle 104 can allow for the two electrodes to be brought together and separated in a motion akin to a pliers or scissors. In some examples, only one of the jaws may be moveable. During a procedure, the one or more electrodes can be brought into proximity to an anatomical target by the operator. Upon location at a desired position, the operator can then initiate the ESU 102 to provide a signal to the electrodes and RF energy can be applied to the anatomical target. As discussed below, the shaft 105 of the RF instrument 101, among other things, protects conductors connecting the electrodes with the ESU 102. Over time, the insulation of the conductors can begin to deteriorate, and an increasing portion of the energy, via leakage current, intended to be distributed by the electrodes can leak via leakage current of the RF signal conducted via the shaft 105. If the leakage current is above a certain level, RF energy may be applied to tissue adjacent the shaft 105 and may cause patient discomfort. In addition, since some energy intended for the one or more electrodes leaks via the shaft 105, the intended procedure can take longer or can be completed using additional wasteful energy. The present inventors have recognized techniques to detect leakage current and modify operator procedures if certain levels of leakage current are detected.

Figure 2:
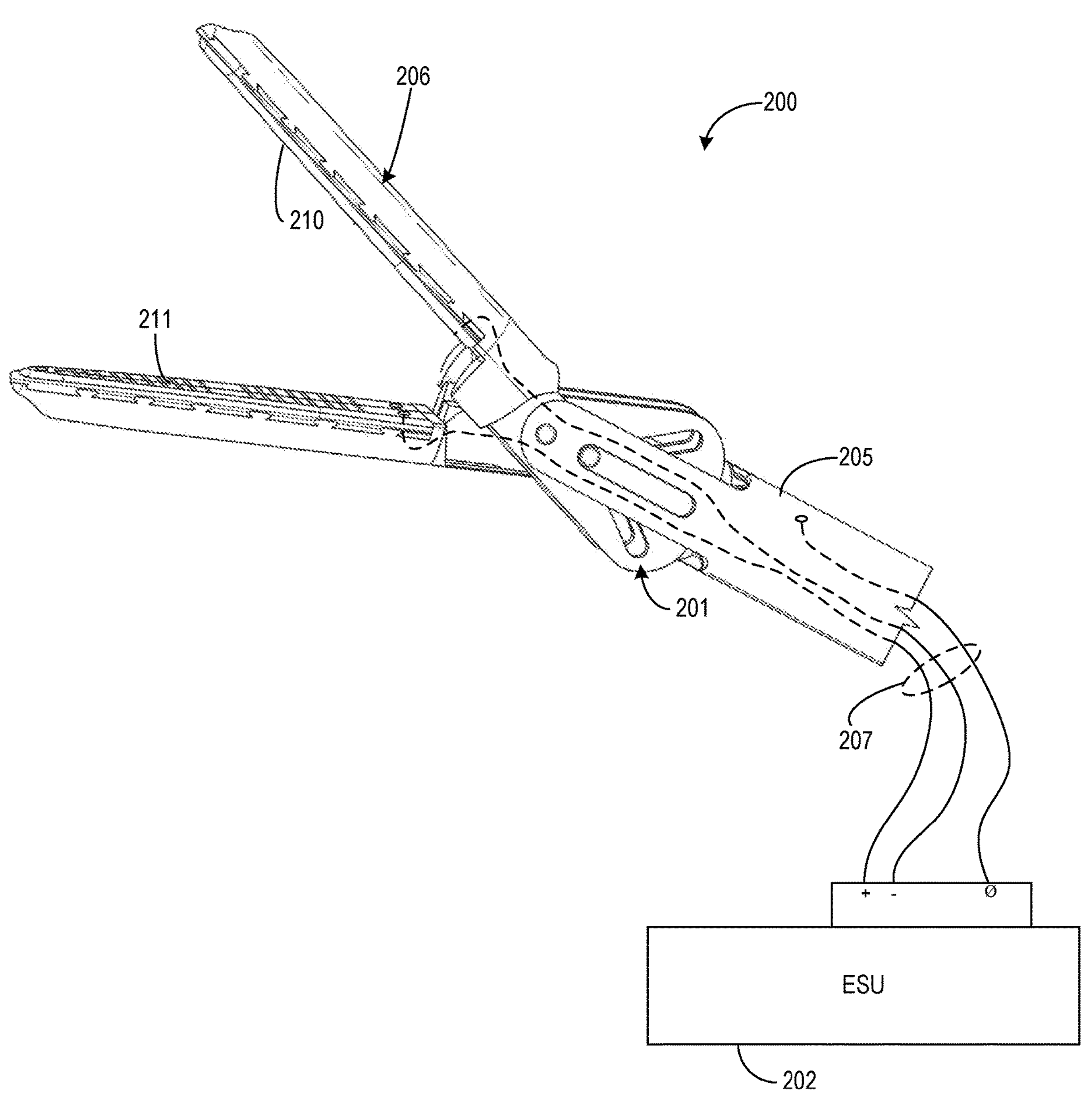
FIG. 2 illustrates a simplified view of an example system to show details of the example leakage current detection.

FIG. 2 illustrates a simplified view of an example system 200 to show details of the example leakage current detection. The system 200 includes a RF instrument 201 and an RF energy source 202. The RF instrument 201 can include a shaft 205 that can extend from a handle (not shown), end effector 206, electrodes 210, 211, and a multiple conductor cable 207 electrically connecting aspects of the RF instrument 201 to the RF energy source 202. In certain examples, the end effector 206 can be mechanically coupled with the shaft 205. The end effector 206 can be used to cut tissue, cauterize tissue, heat tissue, etc. In some examples, the end effector 206 can include a single electrode. In some examples, the RF instrument 201 can include more than two electrodes.

The multiple conductor cable 207 can include a conductor for each electrode, electrode conductors (+, −), and a leakage conductor (Ø) configured to electrically couple to the shaft 205. In certain examples, the shaft 205, or portions of the shaft 205 can be electrically conductive. In some examples, the shaft 205 can be hollow or can form a channel. The conductors (+, −, Ø) of the multiple conductor cable 207 can extend with the shaft 205 and, in some examples, can extend within or coaxially with a hollow shaft 205, or within a channel of the shaft 205. The electrode conductors (+, −) can extend to the electrodes, and during operation can conduct the electrical RF signals of the RF power source 202 to the electrodes (+, −) to generate the RF energy at and about the electrodes 210, 211. The electrode conductors (+, −) can include an exterior layer to insulate the electrode conductors (+, −) from radiating the electrical RF signals except at or about the electrodes 210, 211. However, after repeated use and with age, the exterior layer of the electrode conductors (+, −) can deteriorate. The deterioration can be attributed to age, environment, movement, such as movement during use, or combinations thereof. The deterioration of the exterior layer of the electrode conductors can allow RF energy, manifested as leakage current, to be conducted via the shaft 205 or conductive portions of the shaft 205.

As discussed above, the leakage conductor (Ø) can electrically couple a leakage detection circuit with the shaft 205. The leakage conductor (Ø) can direct leakage current to the leakage detection circuit and, in some examples, can direct leakage RF energy away from tissue not intended to be exposed to RF energy. The leakage detection circuit can measure the leakage current or can compare a level of the leakage current to one or more thresholds to determine whether the leakage current is high enough to inhibit further application of RF energy or to raise an alarm to indicate the leakage current is approaching a level requiring maintenance of the system 200.

Figure 3:
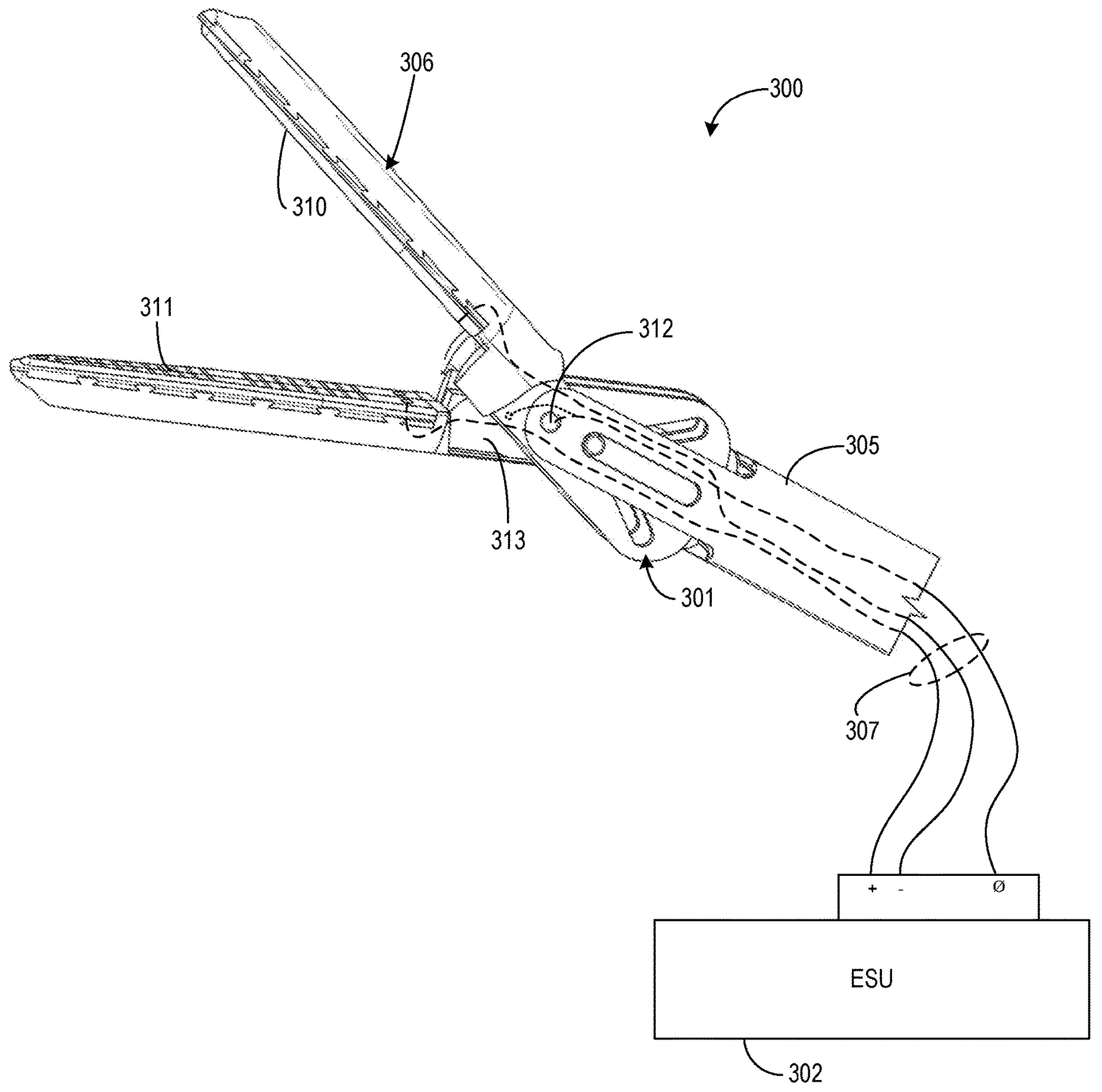
FIG. 3 illustrates a simplified view of an example system to show details of the example leakage current detection.

FIG. 3 illustrates a simplified view of an example system 300 to show details of the example leakage current detection. The system 300 includes a RF instrument 301 and an RF energy source 302. The RF instrument 301 can include a shaft 305 that can extend from a handle (not shown), end effector 306, electrodes 310, 311, and a multiple conductor cable 307 electrically connecting aspects of the RF instrument 301 to the RF energy source 302. In certain examples, the end effector 306 can be mechanically coupled with the shaft 305. The end effector 306 can be used to cut tissue, cauterize tissue, heat tissue, etc. In some examples, the end effector 306 can include a single electrode. In some examples, the RF instrument 301 can include more than two electrodes.

The multiple conductor cable 307 can include a conductor for each electrode, electrode conductors (+, −), and a leakage conductor (Ø) configured to electrically couple to a component of the end effector 306, such as a hinge pin 312 or conductive portion 313 of a jaw of the end effector 306. The conductors (+, −, Ø) of the multiple conductor cable 307 can extend with the shaft 305 and, in some examples, can extend within or coaxially with a hollow shaft 305, or within a channel of the shaft 305. The electrode conductors (+, −) can extend to the electrodes, and during operation can conduct the electrical RF signals of the RF power source 302 to the electrodes (+, −) to generate the RF energy at and about the electrodes 310, 311. The electrode conductors (+, −) can include an exterior layer to insulate the electrode conductors (+, −) from radiating the electrical RF signals except at or about the electrodes 310, 311. However, after repeated use and with age, the exterior layer of the electrode conductors (+, −) can deteriorate. The deterioration can be attributed to age, environment, movement, such as movement during use, or combinations thereof. The deterioration of the exterior layer of the electrode conductors can allow RF energy, manifested as leakage current, to be conducted via conductive portions of the shaft 305, conductive portions of the end effector 306 such as a hinge pin 312, or other conductive components 313 of a jaw of the end effector 306 that are not intended to pass the RF energy.

As discussed above, the leakage conductor (Ø) can electrically couple a leakage detection circuit with the hinge pin 312 or other conductive components 313 of a jaw of the end effector 306. The leakage conductor (Ø) can direct leakage current to the leakage detection circuit and, in some examples, can direct leakage RF energy away from tissue not intended to be exposed to RF energy. The leakage detection circuit can measure the leakage current or can compare a level of the leakage current to one or more thresholds to determine whether the leakage current is high enough to inhibit further application of RF energy or to raise an alarm to indicate the leakage current is approaching a level requiring maintenance of the system 300.

Figure 4:
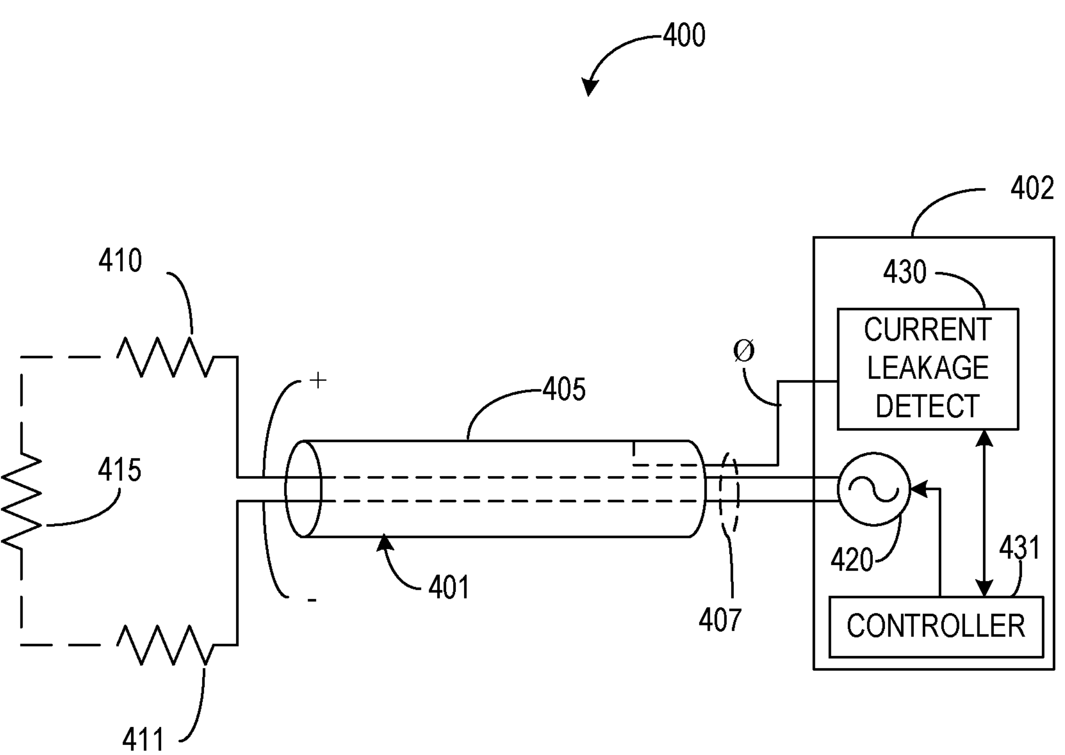
FIG. 4 illustrates generally an electrical model of a system including an example leakage current detector.

FIG. 4 illustrates generally an electrical model of a system including an example leakage current detector. The system can include an RF instrument and a ESU 402. Only certain elements of the RF instrument related to the present subject matter are shown such as a shaft 405, electrodes 410, 411, and conductors (+, −, Ø). In operation, the electrodes 410, 411 can be brought into proximity or into contact with tissue 415 to complete an RF circuit and allow RF energy to be applied to a patient for therapeutic procedures. The RF energy can be generated at the ESU 420. The ESU 402 can include an RF generator 420, a controller 431, and a leakage current detector 430. The RF generator can be electrically coupled to the electrodes 410, 411 via first and second electrode conductors (+, −). A third electrical conductor, or wire, a leakage conductor (Ø), can couple the leakage current detector 430 to components of the RF instrument thru which leakage current may travel should insulation of one of the electrode conductors be damaged, deteriorate or break. One such component of the RF instrument, among others, can be the shaft 405.

Figure 5:
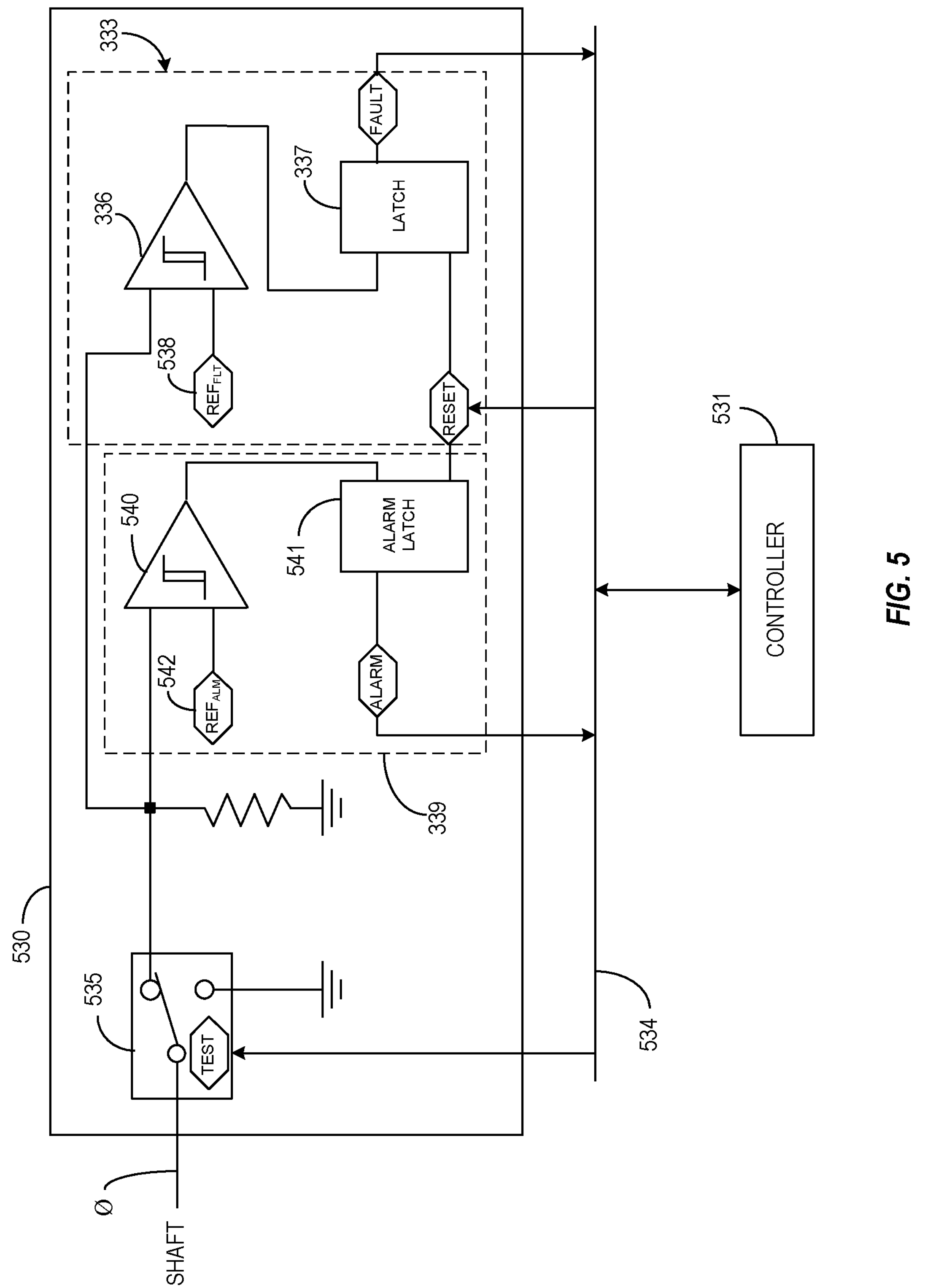
FIG. 5 illustrates generally an example leakage current detection circuit.

FIG. 5 illustrates generally an example leakage current detection circuit 530. The leakage current detection circuit 530 can communicate with a controller 531 such as the controller of an ESU. The leakage current detection circuit can receive the leakage conductor (Ø) from the shaft (e.g., FIG. 2, 205; FIG. 1, 105). In certain examples the leakage current detection circuit can include a sense resistor 532, a fault detection circuit 533 and a controller interface 534. In some examples, the leakage current detector can include a switch 535 to selective couple the leakage conductor (Ø) with the sense resistor, for example, in response to a first state of a test command signal from the controller 531. In certain examples, in response to a second state of the test command signal, the leakage conductor (Ø) can be coupled directly to ground.

The fault detection circuit 533 can include a comparator 536. The comparator 536 can compare a sense voltage developed by any leakage current across the sense resistor 532 to a fault reference 538. If the sense voltage becomes higher than the fault reference ($REF_{FLT}$) 538, the output of the comparator can become active to indicate a fault leakage current condition. In some examples, the controller can coordinate sensing the fault leakage current condition, or lack thereof, with the test command signal. In certain examples, the controller can conduct a leakage current detection test while providing an RF signal to the electrodes. In some examples, the RF signal can be an RF test signal that is not intended to provide substantial therapy but can still provide an indication of leakage current during therapeutic application of RF energy. In some examples, the controller can conduct a leakage current test just before application of therapeutic RF energy. If, during the leakage current test, a fault leakage current condition is indicated, the use of the RF instrument can be terminated. In certain examples, a fault leakage current condition can occur and can last a very short duration. In some examples, the fault detection circuit 533 can include a latch 537 to detect an active state of the output of the comparator 536 and latch the fault leakage current condition. The output (FAULT) of the latch 537 can be provided to the controller via the controller interface 534. In response to a reset command from the controller 531, the latch 537 can be reset to release the fault leakage current condition.

In some examples, the leakage current detection circuit 530 can include an optional alarm detection circuit 539. The alarm detection circuit 539 can include an alarm comparator 540. The alarm comparator 540 can compare a sense voltage developed by any leakage current across the sense resistor 532 to an alarm reference ($REF_{ALM}$) 542. If the sense voltage becomes higher than the alarm reference 542, the output of the alarm comparator 540 can become active to indicate an alarm leakage current condition (ALARM). In some examples, the controller 531 can coordinate sensing the alarm leakage current condition, or lack thereof, with the test command signal. In certain examples, the controller 531 can conduct a leakage current detection test while providing an RF signal to the electrodes. In some examples, the RF signal can be an RF test signal that is not intended to provide substantial therapy but can still provide an indication of leakage current during therapeutic application of RF energy. In some examples, the controller can conduct a leakage current test just before application of therapeutic RF energy. If, during the leakage current test, an alarm leakage current condition is indicated, the use of the RF instrument can be terminated. In certain examples, an alarm leakage current condition can occur and can last a very short duration. In some examples, the alarm detection circuit 539 can include a latch 541 to detect an active state of the output of the alarm comparator 540 and can latch the alarm leakage current condition. The output (ALARM) of the latch 541 can be provided to the controller 531 via the controller interface 534. In response to a reset command from the controller 531, the alarm latch 541 can be reset to release the alarm leakage current condition.

In certain examples, the fault reference ($REF_{FLT}$) 538, the alarm reference ($REF_{ALM}$) 542, or the fault reference ($REF_{FLT}$) 538 and the alarm reference ($REF_{ALM}$) 542 can be set via the controller 331. In certain examples, the alarm reference and the fault reference may be referred to individually as a threshold or a current limit.

Figure 6:
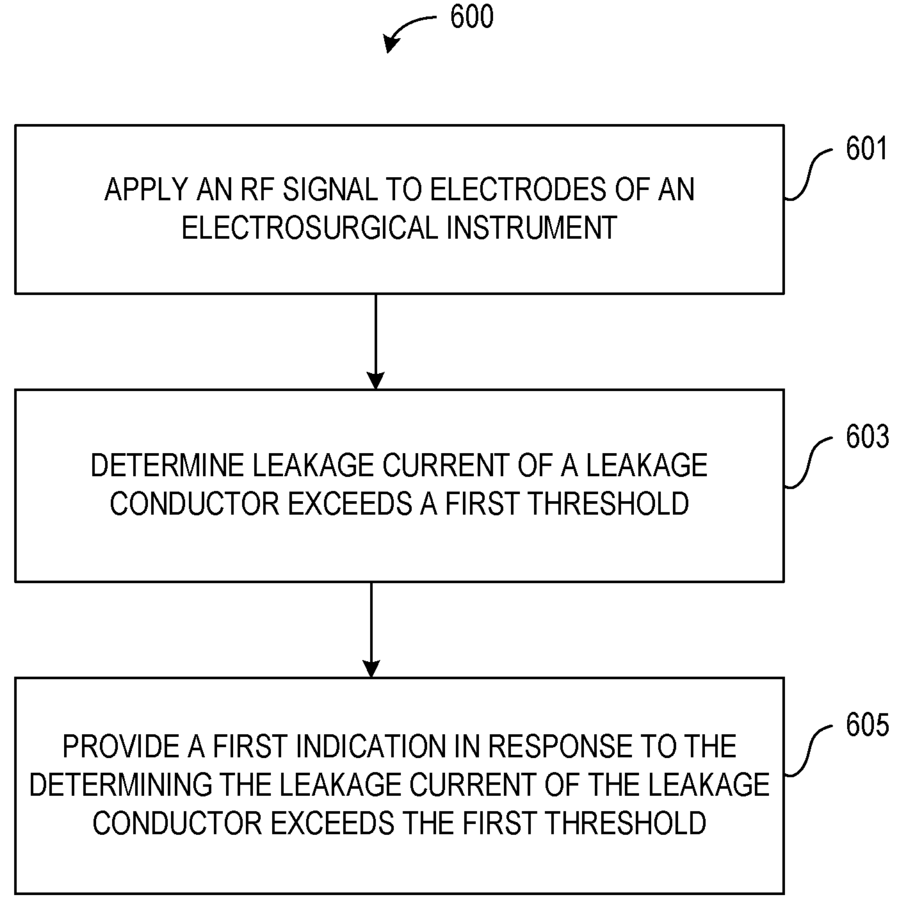
FIG. 6 illustrates generally an example method of operating an electrosurgical instrument.

FIG. 6 illustrates generally an example method 600 of operating an electrosurgical instrument. At 601, an RF signal can be applied to electrode conductors of the electrosurgical instrument. The RF signal can be generated by an RF generator coupled to a controller such as a controller of an ESU. In some examples, the RF signal can be for applying therapy. In some examples, the RF signal can be a test signal. At 603, a leakage current detector can determine whether leakage current of a leakage conductor exceeds a threshold. The leakage conductor can be coupled to components of the electrosurgical instrument that are not designed to provide therapeutic RF energy to a patient and where the capture of leakage current can indicate an electrode conductor has broken, been damaged or has deteriorated to a point of needing repair. Such components can include, but are not limited to metal components such as a shaft of the electrosurgical instrument or linkage components for actuation of one or more jaws. At 605, in response to determining excessive leakage current based on the threshold, an indication can be generated by the leakage current detector. In certain examples, the indication can inhibit further generation or delivery of RF energy from the ESU. In some examples, the leakage current detector can include two thresholds for comparison to the detected leakage current of the leakage conductor. A first threshold can be an alarm threshold to provide an early indication of leakage current exceeding the alarm threshold. The early indication may not inhibit further operation of the ESU but may need to be reset in order to apply subsequent electrosurgical therapy. The second threshold can be a fault threshold and can provide a more persistent indication compared to the alarm indication. The fault indication may terminate generation of RF signals and can inhibit operation of the RF generator until the fault is cleared via a maintenance operation of the ESU of the electrosurgical instrument.

Notes and Examples

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. A system for detecting leakage current, the system comprising:

- a first electrode configured for applying therapy to a patient;
- a support member having a channel, the support member configured to mechanically support the first electrode;
- a first electrical conductor in the form of an insulated wire coupled to the first electrode and configured to couple with an electrosurgical unit (ESU), the first electrical conductor configured to extend from the first electrode to the ESU via the channel;
- a second electrical conductor in the form of an insulated wire electrically coupled to the support member, configured to detect an unintended electrical connection between the first electrical conductor and the support member; and
- a leakage current detector circuit configured to receive and detect current of the second electrical conductor, to compare the detected current to a threshold value, and in response to the detected current exceeding the threshold value, to provide an indication of a leakage current condition.

2. The system of claim 1, wherein the leakage current detector circuit is configured to apply a test signal to the first electrode, to compare current of the second electrical conductor to a current limit in response to the test signal, and to provide the indication in response to the current of the second electrical conductor exceeding the current limit.

3. The system of claim 1, wherein the first electrode is coupled to a first jaw of an electrosurgical instrument, the first jaw mechanically coupled to the support member.

4. The system of claim 1, wherein the ESU includes the leakage current detector circuit.

5. The system of claim 1, including a second electrode mechanically coupled with the first electrode; and

- a third electrical conductor coupled to the second electrode and configured to couple with the ESU, the third electrical conductor configured to extend from the second electrode to the ESU via the channel.

6. The system of claim 5, wherein the leakage current detector circuit is configured to receive the third electrical conductor, to compare current of the third electrical conductor to a second threshold value, and in response to the current of the third electrical conductor exceeding the second threshold value, to provide a second indication of a second leakage current condition.

7. The system of claim 6, wherein the leakage current detector circuit is configured to apply a first test signal to the first electrode, to compare current of the second electrical conductor to a current limit in response to the first test signal, and to provide the indication in response to the current of the second electrical conductor exceeding the current limit.

8. The system of claim 7, wherein the leakage current detector circuit is configured to apply a second test signal to the second electrode, to compare current of the second electrical conductor to the current limit in response to the second test signal, and to provide the second indication in response to the current of the second electrical conductor exceeding the current limit.

9. The system of claim 6, wherein the first electrode is coupled to a first jaw of an electrosurgical instrument, the first jaw mechanically coupled to the support member.

10. The system of claim 9, wherein the second electrode is coupled to a second jaw of the electrosurgical instrument, the second jaw mechanically coupled to the first jaw.

11. The system of claim 1, wherein the leakage current detector circuit includes:

- a sense resistor coupled to the second electrical conductor, wherein the sense resistor is configured to receive the leakage current and generate a voltage at a node of the sense resistor, wherein the voltage at the node represents the leakage current; and
- a comparator configured to receive the voltage at a node of the sense resistor, to receive a voltage representing a current limit reference, and to base the indication on a comparison of the voltage that represents the leakage current with the voltage that represents the current limit reference.

12. The system of claim 11, wherein the leakage current detector circuit includes a latch coupled to an output of the comparator and configured to latch the indication in response to the voltage that represents the leakage current exceeding the voltage that represents the current limit reference.

* * * * *